United States Patent [19]

Marhold et al.

[11] 4,330,366
[45] May 18, 1982

[54] PROCESS FOR THE PREPARATION OF HALOGENATED BENZOYL FLUORIDES

[75] Inventors: Albrecht Marhold, Leverkusen; Erich Klauke, Odenthal, both of Fed. Rep. of Germany

[73] Assignee: Bayer Aktiengesellschaft, Leverkusen, Fed. Rep. of Germany

[21] Appl. No.: 170,448

[22] Filed: Jul. 21, 1980

[30] Foreign Application Priority Data

Aug. 4, 1979 [DE] Fed. Rep. of Germany ....... 2931688

[51] Int. Cl.³ .............................................. C07C 51/58
[52] U.S. Cl. .............................................. 260/544 F
[58] Field of Search ..................................... 260/544 F

[56] References Cited

U.S. PATENT DOCUMENTS 3,336,376 8/1967 Nychka et al. .................. 260/544 F

OTHER PUBLICATIONS

Banks, R. E. "Fluorocarbons and their Derivatives" Oldbourne Press, (London) (1965) p. 139.
Holbrook, G. W. et al. *The Journal of Organic Chemistry*, vol. 31, (1966), pp. 1259-1261.
Patai, Saul "The Chemistry of Acyl Halides" Interscience Publ. (1972), pp. 39-45.
Kirk-Othmer "Encyclopedia of Chemical Technology" Interscience Publ., 2nd Ed. (1964), vol. 5, pp. 357-359.
McBee, E. T. et al. J. Am. Chemical Society (1951), vol. 73, p. 1366.

*Primary Examiner*—Natalie Trousof
*Assistant Examiner*—L. Hendriksen
*Attorney, Agent, or Firm*—Sprung, Horn, Kramer & Woods

[57] ABSTRACT

A process for the preparation of a halogenated benzoyl fluoride, which comprises contacting a halogenated benzotrifluoride of the formula

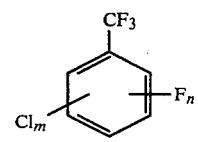

in which
m and n independently of one another represent an integer from 0 to 5, the sum of m and n being 5, with at least one sulphur compound of the formula

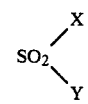

in which
X denotes fluorine, chlorine or hydroxyl and
Y represents hydroxyl, or
X and Y together denote an oxygen atom linked to the sulphur atom by a double bond,
at an elevated temperature, and after reaction with the halogenated benzotrifluoride, removing the sulphur compound from the reaction mixture in the form of a compound of the formula

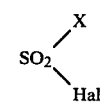

in which
X has the meaning given and
Hal represents fluorine or chlorine, the reaction product is further reacted with potassium fluoride at an elevated temperature and under increased pressure.

8 Claims, No Drawings

PROCESS FOR THE PREPARATION OF HALOGENATED BENZOYL FLUORIDES

The present invention relates to a process for the preparation of halogenated benzoyl fluorides.

It is known that pentafluorobenzoic acid is obtained in 25% yield from pentafluorobenzotrifluoride when this compound is heated under reflux with sulphuric acid for one weeek (J. Am. Chem. Soc. 73, 1366 (1951)).

A process has now been found for the preparation of halogenated benzoyl fluorides, which is characterised in that a halogenated benzotrifluoride of the formula

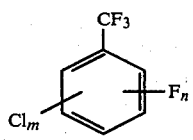  (I)

in which
m and n each, independently of one another, represent an integer from 0 to 5, the sum of m and n being 5,
is reacted with at least one sulphur compound of the formula

  (II)

in which
X denotes fluorine, chlorine or hydroxyl and
Y represents hydroxyl, or
X and Y together denote an oxygen atom linked to the sulphur atom by a double bond,
at elevated temperature, and after reaction with the halogenated benzotrifluoride, the sulphur compound is removed from the reaction mixture in the form of a compound of the formula

  (III)

in which
X has the meaning given and
Hal represents fluorine or chlorine,
and, if appropriate, the reaction product is further reacted with potassium flouride at elevated temperature and under increased pressure.

Halogenated benzotrifluorides which may be mentioned as suitable for the process according to the invention are benzotrifluorides which are penta-substituted in the nucleus by fluorine or chlorine or by fluorine and chlorine, such as pentachlorobenzotrifluoride, pentafluorobenzotrifluoride, tetrachloro-2-fluorobenzotrifluoride, tetrachloro-3-fluoro-benzotrifluoride, tetrachloro-4-fluoro-benzotrifluoride, the isomeric trichloro-difluoro-benzotrifluorides, the isomeric dichlorotrifluoro-benzotrifluorides and the isomeric chlorotetrafluoro-benzotrifluorides.

Examples of sulphur compounds of the formula (II) which may be mentioned as being suitable for the process according to the invention are: fluorosulphonic acid, chlorosulphonic acid, sulphuric acid and sulphur trioxide. The sulphur compounds mentioned can be employed individually or as mixtures. Chlorosulphonic acid or oleum, that is to say a mixture of sulphuric acid and sulphur trioxide, is preferably used. If oleum is used, oleum with a concentration of, for example, 0.1 to 65% by weight of $SO_3$, preferably 10 to 40% by weight of $SO_3$, is suitable.

The amount of sulphur compound of the formula (II) required to achieve as high as possible a yield is at least 1 mol per mol of halogenated benzotrifluoride employed. Preferably, 1 to 3 mols of sulphur compound are employed per mol of halogenated benzotrifluoride. A larger amount of sulphur compound than that indicated is not critical for the success of the process according to the invention, but is of little advantage for economic reasons.

A temperature of 70° to 150° C., preferably 80° to 130° C., may be mentioned as suitable for the process according to the invention.

In the process according to the invention, after reaction with the halogenated benzotrifluoride, the sulphur compound of the formula (II) employed is removed from the reaction mixture in the form of a compound of the formula (III). This removal can be effected, for example, by distillation. Examples of compounds of the formula (III) which may be mentioned are: sulphuryl fluoride, sulphuryl chloride, sulphuryl chloridefluoride, fluorosulphonic acid and chlorosulphonic acid. If sulphuric acid, sulphur trioxide or oleum, that is to say a mixture of sulphuric acid and sulphur trioxide, is used as the sulphur compound of the formula (II), the situation can arise where, when the reaction, according to the invention, with a halogenated benzotrifluoride has ended, this sulphur compound is not present or not entirely present as the compound of the formula (III).

In this case, it is necessary to add an acid halide of carbon, phosphorus or sulphur to the reaction batch when the reaction, according to the invention, with the halogenated benzotrifluoride has ended in order to remove the sulphur compound in the form of a compound of the formula (III). Examples of such acid halides which may be mentioned are the acid fluorides and the acid chlorides, preferably the acid chlorides. Examples of suitable acid chlorides are phosgene, phosphorus trichloride or thionyl chloride, preferably thionyl chloride.

If a higher degree of fluorination of the aromatic nucleus is desired than corresponds to the degree of fluorination of the halogenated benzotrifluoride employed, or if the benzoyl fluoride group formed has been completely or partly converted into a benzoyl chloride group by the use, according to the invention, of an acid chloride of carbon, phosphorus or sulphur, for example thionyl chloride, for the conversion of the sulphur compound of the formula (II) into a compound of the formula (III), the reaction product according to the invention can be further reacted with potassium fluoride at elevated temperature and under increased pressure.

For each replacement of chlorine by fluorine, at least 1 mol of potassium fluoride is necessary to achieve as high as possible a yield. The total amount of potassium fluoride to be employed thus depends chiefly on the number of chlorine atoms to be replaced per mol of halogenated benzoyl fluoride. Thus, for example, to convert pentachlorobenzoyl fluoride into pentafluorobenzoyl fluoride, it is preferable to use 6 to 7 mols of potassium fluoride per mol of the pentachlorobenzoyl fluoride. The use of a larger amount of potassium fluoride than that mentioned does not have an adverse effect, but in general it does not give a higher yield and is thus inexpedient for economic reasons. If, for example, of 5 chlorine atoms bonded to the aromatic nucleus, only 4 are to be replaced by fluorine, it is appropriate to use 4 mols of potassium fluoride per mol of halogenated benzoyl fluoride. In this procedure, a little pentafluorobenzoyl fluoride is formed, but tetrafluorochlorobenzoyl fluoride is obtained as the main product, in addition to only a small amount of products with a lower degree of fluorination. The resulting fluorination mixture can easily be separated by distillation, the desired tetrafluoro-chlorobenzoyl fluoride being obtained as the finished product whilst the products with a lower degree of fluorination can be converted back into the starting material for the process according to the invention. If, in another process variant, about 3 mols of potassium fluoride are employed per mol of pentachlorobenzoyl fluoride, the formation of the pentafluorobenzoyl fluoride is almost completely suppressed. A minor amount of tetrafluoro-chloro-benzoyl fluoride is formed, but trifluorodichloro-benzoyl fluoride is obtained as the main product. In this process variant also, the products can easily be separated by distillation.

To increase the fluorination activity of potassium fluoride, a higher alkali metal fluoride, for example rubidium fluoride or cesium fluoride, preferably cesium fluoride, can be added. The amount of cesium fluoride in the potassium fluoride can be, for example, 0.1 to 99.9 mol%, preferably 0.2 to 10 mol% and particularly preferably 0.5 to 5 mol%, of the mixture of potassium fluoride and cesium fluoride.

The replacement of chlorine by fluorine can be carried out with or without a solvent. The embodiment without a solvent can necessitate somewhat higher reaction temperatures and may have an adverse effect on the yield. The embodiment with a solvent is thus preferred. Examples of solvents which may be mentioned are dimethyl sulphone, N-methyl-pyrrolidone and tetramethylene sulphone, preferably tetramethylene sulphone.

In the preferred embodiment in the presence of a solvent, the replacement of chlorine by fluorine is carried out, for example, at a temperature of 170° to 280° C., preferably 180° to 270° C. A higher temperature within the temperature range mentioned is applicable if a high degree of fluorination is to be achieved. Conversely, the temperature can be somewhat lower within the range indicated if a lower degree of fluorination is to be produced.

The replacement of chlorine by fluorine is carried out under increased pressure, for example under 3 to 20 bars, preferably 5 to 15 bars. This pressure can be achieved, for example, as a result of the autogenous pressure of the reaction mixture. However it can also be favourable to establish the chosen pressure by means of an inert gas, for example nitrogen or argon.

Surprisingly, the halogenated benzoyl fluorides are obtained in good yields in the process according to the invention by simple reactions with generally available chemicals.

The halogenated benzoyl fluorides obtainable in the process according to the invention are valuable intermediate products for the preparation of plant protection agents. Thus, for example, they can be reduced to the halogenated benzyl alcohols by warming to 50° C. with approximately equimolar amounts of sodium borohydride in dioxane as the solvent (German Offenlegungsschrift No. 2,658,074). According to the same German Offenlegungsschrift, by reaction with a substituted cyclopropanecarboxylic acid chloride at 70° to 120° C., for example, these halogenated benzyl alcohols can be converted to the corresponding benzyl ester of the corresponding substituted cyclopropanecarboxylic acid, which in turn are valuable active compounds for combating animal pests of plants, in particular insects and arachnidae.

EXAMPLE 1

(a) 128 g of pentachlorobenzotrifluoride and 145 g of chlorosulphonic acid are initially introduced into an apparatus of high-grade steel. The mixture is warmed to 80° C., whilst stirring, whereupon the evolution of hydrogen fluoride starts. When the evolution of gas subsides, the temperature is further increased to 115° C. and the mixture is then cooled and the excess chlorosulphonic acid and sulphuryl halides which have formed are distilled off under 15 mbars. 88 g of pentachlorobenzyl fluoride (76% of the theoretical yield) of melting point 118° C. are then obtained by distillation under a high vacuum.

(b) 1,184 g of pentachlorobenzoyl fluoride, 1,625 g of dry potassium fluoride and 2,800 ml of tetramethylene sulphone are initially introduced into an autoclave of high-grade steel and a pressure of 8 bars is established by forcing in dry nitrogen. The mixture is then heated at 250° C. for 4 hours, whilst stirring and under the autogenous pressure established, and is cooled and let down. The inorganic salts are filtered off from the reaction batch and the filtrate is distilled over a column. This gives 86 g of pentafluorobenzoyl fluoride (boiling point: 40° to 44° C./16 mbars) and 568 g of a mixture (boiling point: 60° to 90° C./16 mbars) which consists of tetrafluorochlorobenzoyl fluoride (63% by weight) and trifluorodichlorobenzyl fluoride (37% by weight) and can either be separated into the components by distillation or employed for renewed fluorination.

EXAMPLE 2

A mixture of 520 g of 3,5-dichloro-2,4,6-trifluorobenzotrifluoride and 400 g of chlorosulphonic acid is heated for 4 hours, whilst stirring, as described in Example 1. 392 g of 3,5-dichloro-2,4,6-trifluorobenzoyl fluoride (82% of the theoretical yield) of boiling point 90° to 95° C./15 mbars and $n_D^{20}$:1.5007 are obtained by distillation.

EXAMPLE 3

(a) 2,700 g of pentachlorobenzotrifluoride are initially introduced into an apparatus of high-grade steel provided with a stirrer, reflux condenser, metering unit and gas outlet into a washer, and are warmed to 130° C. 1,080 g of 35% strength by weight oleum are then added dropwise in the course of 30 minutes and the mixture is subsequently stirred for about 4 hours until the evolution of gas has ended. Thereafter, it is cooled to about 75° C. and 1,474 g of thionyl chloride are added dropwise. After a further 4 hours and after the evolution of gas has ended, the reflux condenser is replaced by a distillation unit and excess reagents and by-products are distilled off up to an internal temperature of 120° C. A mixture of chlorosulphonic acid and fluorosulphonic acid is then distilled off under a vacuum of about 20 mbars and at an internal temperature of 150°

C. Further distillation under a pressure of 0.1 mbar gives 2,437 g of a mixture of pentachlorobenzoyl fluoride and pentachlorobenzoyl chloride (94% of the theoretical yield) of boiling point 140° to 150° C./0.1 mbar.

(b) 2,400 g of the mixture obtained under (a) are stirred with 3,200 g of dry potassium fluoride and 5,700 ml of tetramethylene sulphone under a nitrogen pressure of 10 bars at 250° C. for 4 hours in an autoclave of high-grade steel, and the mixture is then cooled and let down. The reaction batch is freed from the inorganic salts by filtration and the few impurities are distilled off from the filtrate under a pressure of 20 mbars up to a temperature at which the distillate passes over of 148° C. The distillate collected, which also contains all the tetramethylene sulphone, is stirred with 680 g of dry potassium fluoride again for 4 hours at 250° to 260° C. and under a nitrogen pressure of 10 bars. Renewed distillation gives 487 g of pentafluorobenzoyl fluoride and 208 g of tetrafluorochlorobenzoyl fluoride.

EXAMPLE 4

38 g of sodium borohydride in 200 ml of dry dioxane are initially introduced into the apparatus at 20° C. and a solution of 86 g of pentafluorobenzoyl fluoride in 100 ml of dioxane is added dropwise, whilst stirring. When the addition has ended, the mixture is subsequently stirred at 20° C. for 2 hours and at 80° C. for 30 minutes and cooled and 75 ml of water are slowly added dropwise, followed by dilute hydrochloric acid until the mixture has a clearly acid reaction. After extraction with methylene chloride, the organic phase is distilled. 168 g of pentafluorobenzyl alcohol are obtained at a boiling point of 87° C./19 mbars.

EXAMPLE 5

400 ml of dry dioxane and 55 g of sodium borohydride are initially introduced into a 2 l three-necked flask with a stirrer, reflux condenser and dropping funnel at 20° C., and 247 g of 3,5-dichloro-2,4,6-trifluorobenzoyl fluoride, dissolved in 250 ml of dry dioxane, are then added dropwise at this temperature. When the addition has ended, the mixture is stirred at 20° C. for a further 2 hours and then warmed to the reflux temperature for 1 hour. The solution is cooled to room temperature, a total of 50 ml of water are then added dropwise and the mixture is subsequently rendered acid with dilute hydrochloric acid. The reaction mixture is extracted three times with methylene chloride and, after drying the organic phase over sodium sulphate, the solvent is distilled off. 196.5 g (85% of the theoretical yield) of 3,5-dichloro-2,4,6-trifluorobenzyl alcohol of boiling point 134° to 135° C./20 mbars and melting point 67° to 68° C. are obtained from the residue by further distillation.

What is claimed is:

1. A process for the preparation of a halogenated benzoyl fluoride, which comprises contacting a halogenated benzotrifluoride of the formula

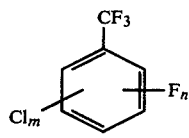

in which
m and n independently of one another represent an integer from 0 to 5, the sum of m and n being 5, with at least one sulphur compound of the formula

in which
X denotes fluorine, chlorine or hydroxyl and
Y represents hydroxyl, or
X and Y together denote an oxygen atom linked to the sulphur atom by a double bond, at an elevated temperature, and after reaction with the halogenated benzotrifluoride, removing the sulphur compound from the reaction mixture in the form of a compound of the formula

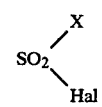

in which
X has the meaning given and
Hal represents fluorine or chlorine.

2. A process according to claim 1 wherein the reaction product is further reacted with potassium fluoride at an elevated temperature and under increased pressure.

3. A process according to claim 1 wherein chlorosulphonic acid is used as the sulphur compound.

4. A process according to claim 1 wherein a mixture of sulphuric acid and sulphur trioxide is used as the sulphur compound and, after the reaction with the halogenated benzotrifluoride, this mixture of sulphur compounds is converted with an acid halide of carbon, phosphorus or sulphur into a compound of the formula

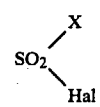

in which
X and Hal have the meaning given in claim 1, and is removed as such from the reaction mixture.

5. A process according to claim 1 wherein pentachlorobenzotrifluoride is reacted with chlorosulphonic acid at 100° to 130° C. and the pentachlorobenzoyl fluoride formed is then further reacted with potassium fluoride in tetramethylene sulphone at elevated temperature and under increased pressure.

6. A process according to claim 1 wherein pentachlorobenzotrifluoride is reacted with a mixture of sulphuric acid and sulphuric trioxide, and, after reaction with thionyl chloride, the sulphuric acid and the oleum, as well as their reaction products, are removed from the reaction mixture by distillation, in the form of compounds of the formula

in which

X and Hal have the meaning given in claim 1.

7. A process according to claim 1 wherein the reaction is conducted at 70° to 150° C.

8. A process according to claim 2 wherein the reaction with potassium fluoride is conducted at 170° to 280° C. at 3–20 bars.

* * * * *